United States Patent [19]

Rose et al.

[11] Patent Number: 5,018,481
[45] Date of Patent: May 28, 1991

[54] INSECT CONTROL DEVICE FOR LIVESTOCK CONTAINING COUMAPHOS

[75] Inventors: Wayne B. Rose, Merriam; Robert G. Arther, Prairie Village, both of Kans.

[73] Assignee: Mobay Corporation, Pittsburgh, Pa.

[21] Appl. No.: 360,495

[22] Filed: Jun. 2, 1989

[51] Int. Cl.$^5$ .............................................. A01K 29/00
[52] U.S. Cl. .................................. 119/156; 424/411; 514/876; 514/920
[58] Field of Search ................ 119/106, 156; 514/876, 514/920, 241; 424/411

[56] References Cited

U.S. PATENT DOCUMENTS

| | | | |
|---|---|---|---|
| 3,852,416 | 12/1974 | Grubb et al. | 424/411 |
| 3,904,746 | 9/1975 | Aries | 119/106 X |
| 4,150,109 | 4/1979 | Dick et al. | 119/106 X |
| 4,158,051 | 6/1979 | Greenberg et al. | 119/106 X |
| 4,189,467 | 2/1980 | von Bittera et al. | 119/106 X |
| 4,195,075 | 3/1980 | Miller | 424/16 |
| 4,265,876 | 5/1981 | Feakins | 424/28 |
| 4,366,777 | 1/1983 | Akhavein et al. | 119/156 |
| 4,428,327 | 1/1984 | Steckel | 119/156 |
| 4,562,794 | 1/1986 | Speckman | 119/156 |
| 4,721,064 | 1/1988 | Denk et al. | 119/156 |
| 4,750,284 | 6/1988 | Parry et al. | 119/156 X |
| 4,837,216 | 6/1989 | Mehlhorn et al. | 514/241 |
| 4,879,117 | 11/1989 | Rombi | 424/411 |

OTHER PUBLICATIONS

John A. Miller et al, Release of Pyrethroids From Insecticidal Ear Tags Journal of Economic Entomology, vol. 76, No. 6, 1335–1340, 1983.

J. Allen Miller et al, Release Rates From Cattle Insecticidal Ear Tags In Various Regions of the U.S., Southwestern Entomologist, vol. 11, No. 1, 3/86, 45–50.

Primary Examiner—Gene Mancene
Assistant Examiner—R. Thomas Price
Attorney, Agent, or Firm—Joseph C. Gil; Lyndanne M. Whalen

[57] ABSTRACT

Annoying insects are controlled by attaching an insect control device to the body of the animal to be treated. The insect control device is a molded article, preferably in the form of an ear tag, which has been formed from a powder mixture of coumaphos, polyvinyl chloride and a plasticizer. The coumaphos is generally used in an amount such that from about 5 to about 30 wt % of the device is coumaphos. Other materials such as lubricants, pigments, stabilizers, etc. may also be included in minor amounts. The device may be formed by any appropriate technique but injection molding has been found to be particularly advantageous.

12 Claims, No Drawings

INSECT CONTROL DEVICE FOR LIVESTOCK CONTAINING COUMAPHOS

BACKGROUND OF THE INVENTION

The present invention relates to insect control devices for livestock and to a process for protecting livestock against insects.

Livestock are frequently troubled by various types of insects such as flies and lice which transmit infection of the skin, eyes and ears as well as cause irritation leading to loss of production. Several approaches have been taken to alleviate this insect problem. One approach requires application of an insecticide spray on the animal. This approach is undesirable because it requires a substantial amount of time and labor to gather the animals to be treated and then to treat the animals. Further, application by this method is effective for only a short period of time so that frequent applications are necessary to effectively treat the livestock. A more economical and less labor intensive approach is therefore generally preferred.

One approach which is used is application of insecticide by having the animal to be treated come into contact with a device from which the selected insecticide is dispensed. Dispensers such as dust bags or oilers are placed in areas where it is anticipated that the livestock will come into contact with them. This approach does reduce the amount of labor involved in treating livestock, but it does not ensure that each animal will receive the necessary treatment at regular intervals.

Another approach employs slow release pesticide technology. In this approach, a pesticide is mixed with a resinous substance which will release the insecticide over an extended period of time. These pesticide containing resins have been used in a variety of forms ranging from collars to tags which should be attached to various body parts of the animal. The use of pesticide containing ear tags is of particular interest for treating livestock as is evident from the large number of publications and patents directed to such ear tags.

For example, U S. Pat. Nos. 4,366,777 and 4,562,794 each disclose ear tags in which a liquid insecticide dispenser is used. In U.S. Pat. No. 4,366,777 the insecticidal liquid which is enclosed in a fibrous or foam reservoir is wicked onto the surface of the tag to provide insecticidal activity. In U.S. Pat. No. 4,562,794, the dispenser or reservoir containing the insecticide is attached to an animal identification tag. Release of the insecticide is dependent upon migration or diffusion of the insecticide through a semipermeable membrane.

U.S. Pat. No. 4,428,327 discloses an insecticide impregnated tape which is attached to a conventional ear tag. Each of these tags has been found to be disadvantageous because the insecticide containing reservoir or tape may be detached from the tag on fences or brush. It would therefore be advantageous to have a tag in which the insecticide is directly incorporated.

Such an approach is disclosed in U.S. Pat. Nos. 4,721,064, 4,195,075 and 4,265,876 as well as in Miller et al, "Release of Pyrethroids from Insecticidal Ear Tags", J. Econ. Entomol. 76:1335-1340 (1983) and Miller et al, "Release Rates From Cattle Insecticidal Ear Tags In Various Regions Of The United States", The Southwestern Entomologist, Vol. 11 No.1, pages 45-50 (March 1986). The Miller et al disclosures and U.S. Pat. No. 4,195,075 are, however, limited to use of liquid insecticides which will evaporate at ambient temperatures. Use of such liquids may be undesirable in areas where the ambient temperature is high enough to cause rapid evaporation of the insecticide and thus result in an undesirably greater release of insecticide over a shorter period of time.

U.S. Pat. No. 4,721,064 teaches that any of the well known migratory and/or vaporizable insecticides may be incorporated in the disclosed tags. Coumaphos is not, however, a migratory or vaporizable insecticide.

U.S. Pat. No. 4,265,876 is limited to tags containing pyrethroid insecticides whereas coumaphos is not a pyrethroid.

SUMMARY OF THE INVENTION

It is an object of the present invention to provide an insect control device for livestock which is effective against arthropods such as flies, grubs, lice, ticks and mites for up to four months.

It is also an object of the present invention to provide a process for protecting livestock against arthropods such as flies, grubs, lice, ticks and mites for up to four months.

These and other objects which will be apparent to those skilled in the art are accomplished by combining coumaphos, polyvinyl chloride and a plasticizer in powder form and then molding this mixture to form an insect control device such as an ear tag. This device or ear tag is attached to the animal to be treated.

DETAILED DESCRIPTION OF THE INVENTION

The insect control devices of the present invention are formed from a mixture of coumaphos, polyvinyl chloride and a plasticizer. Coumaphos is a solid organophosphorous insecticide which is effective against arthropods including flies, grubs, lice, ticks and mites. In the devices of the present invention, coumaphos is generally present in an amount of from 5 to 30 wt % of the total weight of the device and preferably in an amount of from about 10 to about 25 wt %, most preferably in an amount of from 10 to 15 wt %. It is, of course, possible to include other known insecticides in the mixture from which the coumaphos containing insect control devices of the present invention are formed.

Polyvinyl chloride is generally present in the devices of the present invention in an amount of from 50 to 80 wt % of the total weight of the device, preferably in an amount of from about 55 to about 80 wt %, and most preferably from 55 to 65 wt %.

The plasticizer used in making the insect control devices of the present invention may be any of the known plasticizers. Specific examples of suitable plasticizers include: phthalates such as dioctyl phthalate, diphenyl dimethyl phthalate and dihexyl phthalate; sebacates such as dipentyl sebacate, n-butyl benzyl sebacate and dibenzyl sebacate; adipates such as dioctyl adipate, dicapryl adipate, di-isobutyl adipate and dinonyl adipate; hydrogenated polyphenols; alkylated aromatic hydrocarbons; and polyester plasticizers such as polyesters of polyols and polycarboxylic acids having a molecular weight of at least 2000. The plasticizer is present in an amount of from 0 to 30 wt % of the total weight of the insect control device, preferably from about 5 to about 25 wt %, most preferably from 10 to 25 wt %.

Other materials such as dyes, pigments, lubricants, lakes, fillers, anti-oxidants and ultraviolet stabilizers may optionally be included in the mixture from which the insect control devices of the present invention are formed. If these materials are included, they are generally present in an amount of from 1 to 10 wt %, preferably in an amount of from 2 to 4 wt %.

The mixture containing coumaphos, polyvinyl chloride, plasticizer and optional ingredients is a mixture of solids which mixture is molded, preferably by injection molding, to the desired form. The preferred form is an ear tag which may be attached directly to the ear of livestock. Techniques for molding such mixtures are known to those skilled in the art. One such molding method is disclosed in U.S. Pat. No. 4,195,075. Techniques for attaching the molded insect control device to an animal are also well known in the art.

As used herein, the expression "livestock" is intended to include cattle, sheep, pigs, horses and other animals.

Having thus described our invention, the following examples are given as being illustrative thereof. All percentages given in these examples are percents by weight, unless otherwise indicated.

EXAMPLES

EXAMPLE 1

3688 grams of polyvinyl chloride, 1648 grams of coumaphos, 2400 grams of piperonyl butoxide (PBO), 240 grams of organo barium zinc, 12 grams of titanium dioxide and 12 grams of red lake were added in the sequence listed to a mixer where they were mixed for two hours. The resultant plum colored powder mixture was then used to mold (by injection molding) approximately 500 ear tags in which the concentration of coumaphos was 20%.

EXAMPLE 2

3432 grams of polyvinyl chloride, 2064 grams of coumaphos, 2240 grams of dioctyl adipate (DOA), 240 grams of organo barium zinc, 12 grams of titanium dioxide and 12 grams of yellow lake were added in the sequence listed to a mixer where they were mixed for two hours. The resultant light orange colored powder mixture was then molded (by injection molding) into approximately 500 ear tags in which the coumaphos concentration was 25%.

EXAMPLE 3

16.5 pounds (7.5 kg) of coumaphos were mixed with 50 pounds (22.7 kg) of a mixture composed of 200 pounds (90.7 kg) of polyvinyl chloride, 2 pounds (0.91 kg) of epoxidized soybean oil and 30 pounds (13.6 kg) of diethyl phthalate (DEP) in a ribbon blender which was heated to 170° F. This mixture was then extruded at 340° F and the extrudate was injection molded to form ear tags. The coumaphos was present in these ear tags at 25% concentration.

EXAMPLE 4

33.5 pounds (15.2 kg) of coumaphos were mixed with 50 pounds (22.7 kg) of the same polyvinyl chloride containing mixture that was used in Example 3 in a ribbon blender heated to 170° F. This mixture was then extruded and molded in the same manner as the mixture of Example 3. Coumaphos was present in these tags at 40% concentration.

EXAMPLE 5

The ear tags produced in Example 1 were attached to the ears of cattle in herds located in South Texas (28 cattle) and in Georgia (80 cattle). The number of Horn flies on each cow before attachment of the ear tag and at regular intervals subsequent to attachment were counted and the percent reduction of Horn flies was calculated as follows:

$$\text{Percent} = \frac{X \text{ no. flies on untreated animals} - X \text{ no. flies on the ear tag animals}}{X \text{ no. flies on untreated animals}} \times 100$$

The results of these studies are reported in the Table below.

| | # flies pretreatment | |
|---|---|---|
| | South Texas | Georgia |
| | 275 | 100 |
| week # | # flies (% reduction) | |
| 1 | 15 (96.2) | 1.7 (99.0) |
| 2 | 5 (98.2) | — |
| 3 | 3 (98.8) | 0.1 (99.9) |
| 4 | 5 (98.2) | — |
| 5 | 2 (99.3) | 0.3 (99.8) |
| 6 | 2 (99.4) | — |
| 7 | 7 (98.2) | 9.2 (93.8) |
| 8 | 5 (98.6) | — |
| 9 | 12 (96.0) | — |
| 10 | 10 (97.9) | — |
| 11 | 8 (98.4) | 29.7 (81.9) |
| 12 | 12 (98.2) | 17.3 (92.3) |
| 13 | 55 (91.2) | 30.4 (89.2) |
| 14 | 250 (50.0) | 48.6 (85.0) |
| 15 | 350 (50.0) | 70.5 (84.3) |
| 16 | 300 (55.5) | 17.2 (95.5) |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. An insect control device for attachment to livestock which effectively releases insect controlling agent for a period of up to four months comprising a molded article formed from a mixture of coumaphos, polyvinyl chloride and a plasticizer.

2. The device of claim 1 in which the coumaphos is present in an amount of from about 10 to about 25 wt % of the total weight of the device.

3. The device of claim 2 in which the article is in the form of an ear tag.

4. The device of claim 2 in which polyvinyl chloride is present in an amount of from about 50 to about 80 wt %.

5. The device of claim 4 in which the mixture to be molded also includes up to 5 wt % stabilizer.

6. The device of claim 5 in which the mixture to be molded also includes up to 5 wt % pigment or lake.

7. A process for treating livestock to control insects comprising attaching the device of claim 6 to an ear of an animal to be treated.

8. The device of claim 1 in which polyvinyl chloride is present in an amount of from about 50 to about 80 wt %.

9. The device of claim 1 in which the article is in the form of an ear tag.

10. The device of claim 1 in which the mixture to be molded also includes up to 5 wt % stabilizer.

11. The device of claim 1 in which the mixture to be molded also includes up to 5 wt % pigment or lake.

12. A process for treating livestock to control insects comprising attaching the device of claim 1 to an animal to be treated.

* * * * *